United States Patent [19]

Samain et al.

[11] Patent Number: 5,206,156

[45] Date of Patent: Apr. 27, 1993

[54] PROCESS FOR THE PREPARATION OF A PARTICULATE ANTIMICROBIAL PRODUCT, ANTIMICROBIAL PRODUCT OBTAINED AND APPLICATIONS THEREOF

[75] Inventors: Daniel Samain, Toulouse; Frédérique Nguyen, Vaux Sur Mer; Michel Degre, Alzonne, all of France

[73] Assignee: Bio Serae Laboratoires SA, Saint Affrique, France

[21] Appl. No.: 521,977

[22] Filed: May 11, 1990

[30] Foreign Application Priority Data

May 12, 1989 [FR] France .................. 89 06668

[51] Int. Cl.$^5$ .............. C12P 19/04; A61K 37/22; A61K 37/50
[52] U.S. Cl. ............................ 435/101; 435/190; 435/192; 435/264; 424/450; 424/94.1; 424/94.4; 514/54; 252/174.12; 252/DIG. 12
[58] Field of Search .............. 435/101, 190, 192, 264; 424/450, 94.1, 94.4; 514/54; 252/174.12, DIG. 12

[56] References Cited

U.S. PATENT DOCUMENTS

| | | | |
|---|---|---|---|
| Re. 23,523 | 7/1952 | Baker et al. | 424/94 |
| 2,765,233 | 10/1956 | Sarrett et al. | 426/615 |
| 4,233,290 | 11/1980 | Ferrari et al. | 424/94 |
| 4,810,508 | 3/1989 | Dell'Acqua et al. | 426/36 |
| 4,867,990 | 9/1989 | Suwa et al. | 426/8 |
| 4,929,466 | 5/1990 | Knuttsson | 426/615 |
| 4,952,409 | 8/1990 | Bando et al. | 424/450 |
| 4,957,749 | 9/1990 | Prieels et al. | 426/10 |

FOREIGN PATENT DOCUMENTS

| | | |
|---|---|---|
| 0062434 | 10/1982 | European Pat. Off. . |
| 931150 | 7/1963 | United Kingdom . |
| 2185397 | 7/1987 | United Kingdom . |

OTHER PUBLICATIONS

Chemical Abstracts, vol. 85, No. 25, Abstract No. 190934h.
Hatsuda, Kazuyoshi, Chemical Abstracts, vol. 114, #59713k; p. 471.

*Primary Examiner*—Johnnie R. Brown
*Assistant Examiner*—Pamela S. Webber
*Attorney, Agent, or Firm*—Harold H. Dutton, Jr.

[57] ABSTRACT

The invention relates to a process for the preparation of a particulate antimicrobial product from the LP system of the lactoperoxidase enzyme/oxygen donor/oxidizable substrate (if needed). The process comprises bonding the lactoperoxidase enzyme to a particulate carrier comprising a polysaccharide nucleus, a first lipidic layer and a second phospholipidic layer in such a manner that the enzyme molecules are inserted into this second layer and/or into the first layer. The product according to the invention is obtained by then conditioning in a non-aqueous medium the aforesaid particulate vector and the molecules of the LP system not integrated into said vector. The process of the invention permits adjusting the diffusability of the product and its mobility as a function of the intended applications, without destruction of the LP system.

13 Claims, No Drawings

PROCESS FOR THE PREPARATION OF A PARTICULATE ANTIMICROBIAL PRODUCT, ANTIMICROBIAL PRODUCT OBTAINED AND APPLICATIONS THEREOF

This invention relates to a process for the preparation of a particulate antimicrobial product starting from an antimicrobial system comprising the enzyme lactoperoxidase, an oxygen donor and if needed, an oxidizable substrate. The invention also provides the particulate product obtained by carrying out the process, and applications thereof in the fields of pharmaceuticals, hygiene, disinfection and preservation.

BACKGROUND AND OBJECTS OF THE INVENTION

The antimicrobial enzyme system of lactoperoxidase/oxygen donor/oxidizable substrate, hereinafter referred to as the "LP system," is known for its antimicrobial properties. This system is contained in the primary secretions of mammals (milk, saliva tears, etc) and assures their protection as well as the protection of mucous membranes. However, this LP system which is present in the form of small size molecules is very soluble in aqueous media, such that in a humid environment or in contact with a hydrated body, it is not possible to limit its diffusion in order to concentrate its action in a given area. Further, its recovery requires very sophisticated separation techniques.

The present invention seeks to provide, starting from the LP system, a particulate product of which the proteic components are insoluble in aqueous media, and their mobility and the diffusability may be adjusted as a function of their application.

A primary object of the invention is to obtain the aforesaid particulate product without denaturation of the LP system, or chemical alteration of the one or more enzymes of the system.

Another object of the invention is to permit imparting to the particulate product complementary properties (electric charges . . . ) adapted to the intended applications.

DESCRIPTION OF THE INVENTION

The preparation process according to the invention utilizes the aforesaid LP system in which the oxygen donor may be either a peroxide, or reactive substances, one of which may be an enzyme (glucose oxidase, xanthine-oxidase . . . ), or micro-organisms (lactobacilli, lactic streptococci . . . ). This LP system may, but need not, comprise an oxidizable substrate depending upon the intended application (thiocyanate, salt of iodine or bromine . . . ). This substrate is not necessary in the case of an application in a medium already containing such an oxidizable substrate in a sufficient quantity. The process of the invention is characterized in:

binding at least the lactoperoxidase enzyme of the LP system on a particulate vector or carrier, of which each particle comprises a nucleus constituted by a hydrophilic, polysaccharidic polymer, a first lipidic layer chemically bound to the nucleus by the hydroxyl functions or derivative functions, and a second phospholipidic layer, of a type such that the enzyme molecules are inserted into the second phospholipidic layer and/or into the first lipidic layer, conditioning in a non-aqueous medium the aforesaid particulate vector and the molecules of the LP system not integrated in said particulate vector.

In the case in which the oxygen donor contains as an active substance an oxidase enzyme, this is also preferably bonded to the particulate vector.

Thus, the process of the invention leads to a particulate antimicrobial product in which one or more enzymes are bound to a particulate vector which is insoluble in aqueous medium, and the size and density of which may be adjusted by an appropriate selection of the polysaccharidic nucleus. It should be noted that the carrier comprises biocompatible and ingestible elements (particularly metabolizable without residue) which permits a utilization of the product in medical and food applications.

It has been verified experimentally that the binding of the enzyme in the lipidic and phospholipidic layers is stable under normal conditions of use, the product having no tendency to release them. These enzymes situated on the surface of the vector and not denatured, retain their enzymic activity for catalyzing the oxidation reaction of the substrate by the oxygen donor, which leads to the known antimicrobial action of the LP system. This activity is maintained integrally or quasi-integrally with, however in most of the cases, a reduced reaction rate, due to the lower mobility of the components.

However, in an unexpected manner, the in vitro kinetics do not seem to be affected in the case in which one grafts ionic functions onto the surface of the polysaccharide nucleus at the moment when the first lipidic layer is formed. The subjacent ionic character thus conferred to this first lipidic layer seems to have a favorable effect on the enzymatic activity of the lactoperoxidase which offsets the reduced reaction rate. This effect is presently difficult to explain, has been measured by the chlorimetric method with orthophenylene diamine (constituting the oxidizable substrate), the donor for these measures being a peroxide.

The process of the invention may be used for preparing an LP system reinforced by lactoferrine LF, this latter being also bound to the particulate vector. In the same manner, additives may be adjusted to the system, and in particular a superoxydismutase 50D enzyme having a protective function in the medium, this enzyme being also bound to the particulate vector.

Preferably, each enzyme is bound independently to the particulate vector in such a manner that each particle carries a single enzyme, the particulate products thus prepared being then mixed with each other and with other products of the LP system.

In certain applications, it is desireable to slow the activation of the compounds in order to avoid a loss of activity away from the site of the application. In this case, according to one embodiment possible for the process, after the binding, the particles of the particulate vector ar coated with a surface layer of polyoloside or of a colloidal substance. In a non-aqueous medium, this surface layer isolates the different reactive substances which will be able to be mixed long before the use of the product, the activity being initiated at the time of use by hydration and solubilization of the surface layer of polyoloside. The coating by means of this layer may be carried out by conventional dipping or spraying processes.

According to another embodiment, electrically charged amphiphilic molecules may be inserted into the second phospholipidic layer of the particulate vector, in order to confer an electrical charge on the particles. It is thus possible to favor, or on the contrary to disfavor, the phenomena of aggregation or adhesion of said particles, either on the surfaces, or with other particles in suspension, or even with solubilized molecules.

The method for binding onto the particulate vector of the one or more enzymes to be bound may be that described in French patent application No. 88.07110. This binding is in particular achieved:

firstly, by grafting the lipidic layer about the polysaccharide nucleus in an aprotic medium which is a nonsolvent of the polysaccharides, for forming an acylated nucleus, then placing in the presence of said acylated nucleus, one part of the phospholipids of the second layer, and the one or more enzymes to be bound, and by hydrating the composite at a temperature approximately equal to the transition temperature of the phospholipids.

In the case of a lipidic layer of a subjacent ionic nature, the grafting of this layer onto the polysaccharidic nucleus comprises causing the polysaccharidic nucleus to react with a mixture of a chloride of a fatty acid and an anhydride of a dicarboxylic acid in a minor proportion, in particular with succinic anhydride.

In practice, the dicarboxylic acid anhydride is mixed in a molar proportion less than 40% with respect to the fatty acid chloride (stearic chloride or the like) in order to retain a sufficiently lipidic character in order that the second phospholipidic layer will adhere.

The polysaccharidic nucleus is in each case selected as a function of the application. It may be natural, its insolubility being due to its chemical nature (cellulose, certain varieties of starches such as amylopectin, . . . ) or alternatively obtained by synthetic reticulation (dextran, beta-amylose, . . . ). The desired size is obtained by appropriate grinding and screening. In the case of reticulated nuclei, their density may be adjusted while causing the degree of reticulation to vary during the polymerization. The size of said polysaccharidic nuclei may vary between $10^{-8}$ m and $10^{-5}$ m, the small sizes being interesting in the case of medications for enabling a certain diffusion (for example, for passing through a barrier such as the skin), the large sizes being interesting for preventing diffusion in order to concentrate the activity and to permit, in certain cases, a recovery of the enzymes by physical means (filtration, centrifugation, decantation, . . . ). In the case of moist nuclei, a drying thereof will be carried out before fixing of the first layer, drying which may, for example, be carried out by atomizing after polymerization and fragmentation in order to avoid the formation of aggregates.

The first lipidic layer is grafted in a medium which is a non-solvent (vis-a-vis the polysaccharidic nuclei), especially dichloromethane: the compounds, constituted by the nuclei, an acid chloride or an acid anhydride (particularly stearic) and a tertiary amine serving as a catalyst (for example triethylamine) are dispersed in this medium in such a manner as to produce an acylation reaction on the periphery of each nucleus. The thickness of this layer may be adjusted by adapting the stoichiometry and the duration of the reaction. Preferably, these conditions are adapted to obtain a very thin layer, in particular a monomolecular layer which suffices to assure the binding of the second layer and the enzyme. Moreover, the quality of the binding and the maintenance of the enzymic activity appears favored by grafting of long chain fatty acids of a chain length comprising between 14 and 22, to avoid a stiffening of said layer above this number. In particular, C18 fatty acids (stearic acid) gives excellent results. As already indicated, a subjacent ionic character may be confered on this first layer by adding succinic anhydride in a minor amount in the medium.

The second phospholipidic layer is preferably produced from phospholipids of animal or vegetable origin such as soy lecithin, egg lecithin, milk lecithin. This second layer may be produced by mixing the acylated nuclei, the phospholipids and the enzymes to be bound, in water kept at the transition temperature of the phospholipids, and with agitation. The duration of the formation of said layer is on the order of 30 to 60 minutes. The stoichiometry is adapted as a function of the size of the acylated nuclei, for obtaining a monolayer of phospholipid (a molecular layer). This layer has a double role:

permitting the particles to be dispersed in a homogeneous mannerin aqueous medium (which will not be the case in the presence of the single first layer strictly hydrophobic, and improving the binding of the enzyme (or other elements).

The invention also relates to a new product, a particulate antimicrobial product obtained by carrying out the aforesaid process. This product comprises an enzyme lactoperoxidase, an oxygen donor and, if desired, an oxidizable substrate, and is characterized in that at least the enzyme lactoperoxidase of the system is bonded to a particulate carrier or vector, each particle of which comprises a nucleus formed of a hydrophilic polysaccharidic polymer, a first lipidic layer chemically bound to the nucleus by hydroxyl functional groups or derivative functional groups, and a second phospholipidic layer, the molecules of the enzyme being inserted into the second phospholipidic layer and/or into the first lipidic layer.

The invention extends as well to compositions for the application of the aforesaid product, in particular:

a medicamentous composition for the treatment of skin, mucous membranes or the digestive tract, a composition for the microbial decontamination of products or materials, an antiseptic dentifrice.

The particulate product according to the invention associates the following properties which make it well suited to these applications:

effective antimicrobial activity, biocompatibility and biomimetic character (analogous to the second layer with the cellular membrane itself permitting interaction with the latter and maintaining the enzymatic activity at the surface, even of tissues), limited diffusion and excellent stability.

DETAILED DESCRIPTION OF PREFERRED EMBODIMENTS

The description which follows provides examples of embodiments which illustrate the process of the invention and the performance of the particulate products obtained.

EXAMPLE 1

This example shows the preparation of a particulate antimicrobial product of a relatively high granulometry (from $10^{-6}$ to $3.10^{-6}$ m) for presenting a slow diffusion rate.

PREPARATION OF THE POLYSACCHARIDIC NUCLEUS

In a balloon of 1 liter, 150 g of starch of the betaamylose type are mixed with 150 ml of a solution of sodium epochlorohydrin, and agitated vigorously for 5 minutes, heated to 80° C. and allowed to polymerize at 80° C. for 10 hours. A reticulated gel is obtained, which is washed and replaced in suspension in 2 l of water, then mechanically ground (in a helical grinder) and then sifted by centrifuging to achieve a granulometry comprising between $10^{-6}$ and $3.10^{-6}$ m.

The product is dried by spraying and relatively flexible spheriodal particles are obtained by reason of a slightly elevated degree of reticulation.

GRAFTING OF THE FIRST LIPIDIC LAYER 100 g of the proceeding particles are dispersed in 1 liter of dichloromethane. Next are added to the medium 25 g of triethylamine and 60 g of stearic acid chloride. This mixture is agitated slowly at 37° C. for 24 hours. The particles are decanted and they are washed with ethanol.

An analysis by the "Lauwerys" method shows that the stearic acid (C18) is bonded to the nucleus by ester functional groups derived from the hydroxyl functional groups of the nucleus, with a weight proportion of 2% of the acid with respect to the nucleus. This proportion is characteristic of a monomolecular layer. The particles obtained have a strongly hydrophobic character which reflects the character of total acylation.

BINDING OF THE LACTOPEROXIDASE AND FORMATION OF THE SECOND LAYER

From the lactoperoxidase is extracted a bovine lactoserum by ion exchange chromatography. This lactoperoxidase of purity greater than 95% is lyophilized in order to be very dry and stable.

In this example, the LP system is comprised of lactoperoxidase, potassium thiocyanate as the oxidizable substrate, and by the glucose oxidase system as an oxygen donor, only the lactoperoxidase being bonded to the particulate vector.

In a 1 liter flask is placed 2 g of the acylated polysaccharide nuclei previously prepared, 0.2 g of lactoperoxidase lyophilizate and 0.2 g of hydrogenated lecithin (animal origin: hen eggs subjected to a hydrogenation step). The mixing is carried out to dryness and 400 ml of distilled water is added by small amounts with agitation. The suspension is incubated at 37° C. (transition temperature of the lecithin) for 30 minutes.

One part of the suspension is centrifuged to separate the particles of the medium and the enzymatic activity of the lactoperoxidase thus bonded is analyzed by the orthophenylene diamine method. It is determined that the percentage of non-bonded enzyme on the vector (remaining in solution) is 0.5% (very low loss) and that the enzymatic activity is equivalent to 60% of the activity of the same quantity of lactoperoxidase in the free state. These results are quite satisfactory and show that the lactoperoxidase is neither denatured nor masked by the vector (the reduction in activity coming from, essentially, the less mobility and therefor a reduction of the kinetics).

The other part of the suspension is lyophilized and mixed with the other constituents of the LP system: potassium thiocyanate (commercially available dry powder) and the glucose-oxidase system (also commercially available and in the form of a powder), in the following weight percentages:

44.20% of the particulate vector bearing the lactoperoxidase, 11.06% of potassium thiocyanate, 44.20% of glucose, 0.44% of the oxidase.

The granular product thus prepared has been used after hydration for testing its antimicrobial action on bacteria of the genus Listeria. A comparative count with control cultures has shown that the antimicrobial activity if very effective (total destruction of the Listeria after 4 hours of incubation at 37° C., while the population of the control is maintained.

EXAMPLE 2

The polysaccharidic nuclei are the same as previously in Example 1.

The acylation is done with the same procedure but with a lesser quantity of stearic acid chloride, 48g, while adding 4 g of succinic anhydride in order to provide an ionic acidic character subjacent to the first lipidic layer.

The rate of fatty acid obtained in this case is 1.6%: the monolayer is composed by the fatty acids with certain sites occupied by monoesters of the succinic acid.

The second phospholipidic layer and the binding of the lactoperoxidase are carried out as in Example 1.

Analyses have shown in this case that the percentage of enzyme not bound to the vector is slightly less (0.35%) and especially that the enzymatic activity is equivalent to 100% of that of the same quantity of enzyme in the free state. These tests seem, therefor, to demonstrate an activation effect on the enzymatic activity of the lactoperoxidase by the partial ionization of the first layer.

The particulate antimicrobial product is prepared as before from the aforementioned particles and the other components of the LP system.

EXAMPLE 3

The suspension of the biovector loaded with lactoperoxidase produced in Example 1 is recovered before lyophilization. Mannitol is added thereto in an amount by weight equal to double the weight of the vector. The mixture is mixed with stirring in order to dissolve the mannitol and the suspension is atomized at low temperature (35° C.).

particles are obtained in which the second layer is covered with a skin covering the mannitol, which masks the enzymatic effect while this very water soluble skin is not dissolved by hydration.

The particulate antimicrobial product is then prepared with the other components as before. Its stability in non-aqueous media is very good, no loss of activity being determined over long periods of storage.

While this invention has been described as having certain preferred features and embodiments, it will be understood that the invention is capable of still further variation and modification, without departing from the spirit of the invention, and this application is intended to cover andy and all variations, modifications and adaptations of the invention which fall within the spirit of the invention and the scope of the appended claims.

We claim:

1. A process for preparation of a particulate antimicrobial product using the antimicrobial LP system of lactoperoxydase enzyme/oxygen donor/oxidizable substrate, wherein the oxygen donor is a peroxide, a reactive substance, or micro-organisms, for modifying the physiochemical properties of the LP system and providing the LP system in the form of particles insoluble in an aqueous medium, the process comprising:

bonding at least the lactoperoxydase enzyme of the LP system to a particulate vector, each particle of said particulate vector comprising a nucleus formed of a hydrophilic polysaccharidic polymer, a first lipidic layer chemically bound to the nucleus by hydroxy functional groups or derivatives thereof, and a second phospholipidic layer so that the molecules of enzyme are inserted into the second phospholipidic layer and/or into the first lipidic layer, introducing said particulate vector into a non-aqueous medium.

2. A preparation process as in claim 1, in which the oxygen donor comprises as an active substance an oxidase enzyme, and bonding onto the particulate vector said oxidase enzyme molecules.

3. A process as in claim 1 for the preparation of an LP system strengthened by lactoferrine LF, comprising bonding the LF onto the particulate vector.

4. A process as in claim 1 for the preparation of an LP system containing as a protector of the medium an enzyme superoxidase SOD, comprising bonding the SOD into the particulate vector.

5. A process for preparation as in claim 1, comprising grafting onto the surface of the polysaccharide nucleus ionic functional groups at the same time as the formation of the first lipidic layer for confering an ionic character upon said lipidic layer.

6. A preparation process as in claim 1 comprising inserting electrically charged molecules into the second phospholipid layer on the particulate vector.

7. A preparation process as in claim 5, and comprising producing the bonding to the particulate vector by grafting the lipidic layer to the polysaccharide nucleus in an aprotic medium which is a non-solvent for the polysaccharides for forming an acylic nucleus, placing the phospholipids of the second layer and the one or more components of the LP system elements in the presence of said acylated nucleus, and hydrating the same at a temperature near the transition temperature of the phospholipids.

8. A preparation process as in claim 7, including grafting onto the saccharidic nucleus, the lipidic layer and its ionic functional groups by causing a reaction of the polysaccharidic nucleus with a mixture of a fatty acid chloride and a dicarboxylic acid anhydride in a minor amount.

9. A preparation process as in claim 1 including, after the bonding, covering the particles of the particulate vector by means of a surface layer of polyoloside or a colloidal substance.

10. A preparation process as in claim 1 in which the nucleus is produced from a polysaccharidic polymer selected from the group consisting of starch, dextran and cellulose.

11. A preparation process as in claim 1 in which the first lipidic layer is produced by the reaction of a chloride or an acid anhydride, catalyzed by a tertiary amine, these compounds being dispersed in dichloromethane at the same time as the saccharidic nuclei.

12. A preparation process as in claim 11, and including using for producing the first layer a compound selected from the group consisting of chlorides and anhydrides of long chain fatty acids of between 14 and 22 carbon atoms.

13. A preparation process as in claim 1 in which the second phospholipidic layer is produced from phospholipids of animal or vegetable origin selected from soy lecithin, egg lecithin, or milk lecithin.

* * * * *